US009504663B2

(12) United States Patent
Freissmuth et al.

(10) Patent No.: US 9,504,663 B2
(45) Date of Patent: Nov. 29, 2016

(54) COMPOSITION FOR THE TREATMENT OF CYSTIC FIBROSIS

(75) Inventors: Michael Freissmuth, Vienna (AT); Christina Gloeckel, Vienna (AT); Xaver Koenig, Vienna (AT); Simon Keuerleber, Vienna (AT)

(73) Assignee: SciPharm SaRL, Junglinster (LU)

(*) Notice: Subject to any disclaimer, the term of this patent is extended or adjusted under 35 U.S.C. 154(b) by 0 days.

(21) Appl. No.: 13/982,399

(22) PCT Filed: Feb. 3, 2012

(86) PCT No.: PCT/EP2012/051880
§ 371 (c)(1),
(2), (4) Date: Aug. 7, 2013

(87) PCT Pub. No.: WO2012/107363
PCT Pub. Date: Aug. 16, 2012

(65) Prior Publication Data
US 2014/0018430 A1    Jan. 16, 2014

(30) Foreign Application Priority Data

Feb. 7, 2011 (EP) .................................... 11153541

(51) Int. Cl.
| A61K 38/00 | (2006.01) |
| C07K 14/47 | (2006.01) |
| A01N 37/10 | (2006.01) |
| A61K 31/19 | (2006.01) |
| A61K 31/192 | (2006.01) |
| A61K 31/4166 | (2006.01) |
| A61K 31/437 | (2006.01) |
| A61K 31/44 | (2006.01) |
| A61K 31/5575 | (2006.01) |
| A61K 31/5578 | (2006.01) |
| A61K 31/5585 | (2006.01) |
| A61K 45/06 | (2006.01) |

(52) U.S. Cl.
CPC ......... A61K 31/192 (2013.01); A61K 31/4166 (2013.01); A61K 31/437 (2013.01); A61K 31/44 (2013.01); A61K 31/5575 (2013.01); A61K 31/5578 (2013.01); A61K 31/5585 (2013.01); A61K 45/06 (2013.01)

(58) Field of Classification Search
None
See application file for complete search history.

(56) References Cited

U.S. PATENT DOCUMENTS

| 2001/0006979 A1 | 7/2001 | Stratton et al. |
| 2005/0101608 A1* | 5/2005 | Santel ..................... 514/252.16 |
| 2006/0083714 A1 | 4/2006 | Warner |
| 2007/0249668 A1 | 10/2007 | Sprague et al. |
| 2009/0221570 A1 | 9/2009 | Haning et al. |
| 2009/0325976 A1 | 12/2009 | Tung |

FOREIGN PATENT DOCUMENTS

| DE | 102005016345 | | 10/2006 |
| JP | 2007506752 | A | 3/2007 |
| JP | 2008534634 | A | 8/2008 |
| JP | 2010513533 | A | 4/2010 |
| JP | 2010518122 | A | 5/2010 |
| JP | 2013501032 | A | 1/2013 |
| JP | 2013515023 | A | 5/2013 |
| WO | 99/18095 | A1 | 4/1999 |
| WO | 99/18099 | A1 | 4/1999 |
| WO | 00/50402 | A1 | 8/2000 |
| WO | 01/64639 | A2 | 9/2001 |
| WO | 02/085906 | A1 | 10/2002 |
| WO | 03/030912 | A1 | 4/2003 |
| WO | 03/070279 | A1 | 8/2003 |
| WO | 03/074055 | A1 | 9/2003 |
| WO | 2006/014930 | A2 | 2/2006 |
| WO | 2007/050783 | A2 | 5/2007 |
| WO | WO2008009816 | | 1/2008 |
| WO | 2008/079383 | A1 | 7/2008 |
| WO | WO 2008130619 | A2 * | 10/2008 |
| WO | WO2010106494 | | 9/2010 |

OTHER PUBLICATIONS

Tissieres et al., Aerosolized Iloprost as a Bridge to Lung Transplantation in a Patient With Cystic Fibrosis and Pulmonary Hypertension, 2004, Ann Thorac Surg, vol. 78, pp. e48-50.*
Response to the Communication pursuant to Rules 161(1) and 162 EPC, European Patent Application 12704027.7-1464, Apr. 7, 2014.
Product Insert for KALYDECO (ivacaftor), Vertex Pharmaceuticals Inc., Feb. 2014.
International Search Report, International Patent Application No. PCT/EP2012/051880, Mar. 12, 2012.
International Written Opinion, International Patent Application No. PCT/EP2012/051880, Mar. 12, 2012.
European Search Report, European Patent Application No. 11153541.5, Apr. 21, 2011.
Tissieres P. et al., Ann Thorac Surg, 2004, vol. 78, No. 3, e48-e50.

(Continued)

Primary Examiner — Kortney L Klinkel
Assistant Examiner — Tori M Strong
(74) Attorney, Agent, or Firm — Loza & Loza, LLP; Michael F. Fedrick

(57) ABSTRACT

The present invention provides a composition comprising at least one prostacyclin or prostacyclin analog or a pharmaceutically acceptable salt thereof and at least one phosphodiesterase (PDE) 4 inhibitor and optionally a further PDE inhibitor for use in preventing or treating cystic fibrosis by selectively increasing the cAMP levels in bronchoepithelial cells.

13 Claims, 6 Drawing Sheets

(56) References Cited

OTHER PUBLICATIONS

Figure 1:
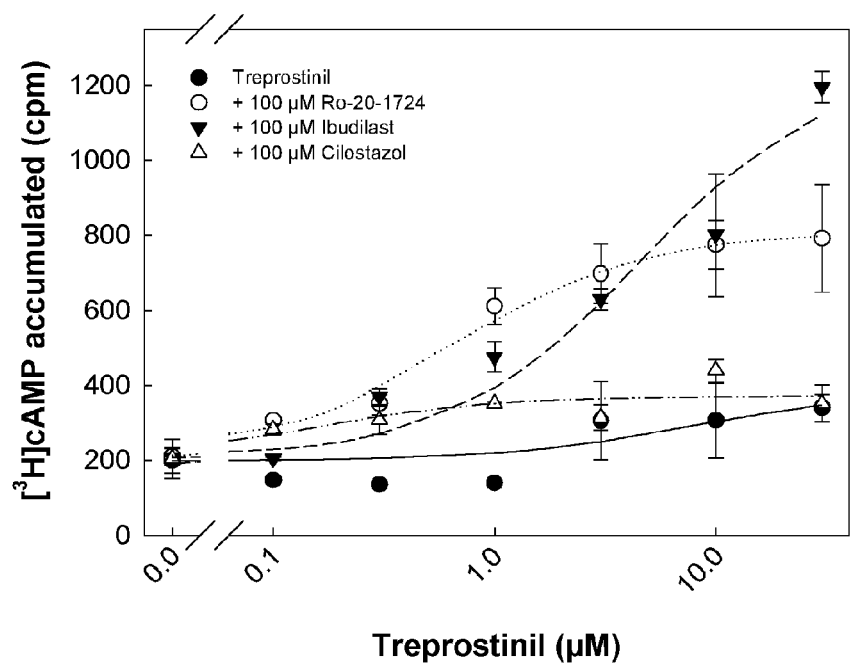

Cobb B.R. et al., Am J Respir Cell Mol Biol, 2003, vol. 29, pp. 410-418.
Lubamba B. et al., Am J Respir Crit Care Med, 2008, vol. 177, No. 5, pp. 506-515.
Clarke L. L., J Respir Crit Care Med, 2008, vol. 177, pp. 469-470.
Aronoff D.M. et al., J Immunol, 2007, vol. 178 pp. 1628-1634.
Bender A.T. et al, Pharmacol Rev, 2006, vol. 58, No. 3, pp. 488-520.
Francis S.H. et al., Physiol Rev, 2011, vol. 91, pp. 651-690.
Hetman J.M. et al., PNAS, 2000a, vol. 97, No. 1, pp. 472-476.
Hetman J.M. et al., PNAS, 2000b, vol. 97, No. 23, pp. 12891-12895.
Houslay M.D. et al., Drug Discov Today, 2005, vol. 10, No. 22, pp. 1503-1519.
Omori K. et al., Circulation Research, 2007, vol. 100, pp. 309-327.
Nikam V.S. et al., Am J Respir Cell Mol Biol, 2011, vol. 45, pp. 692-703.
Soderling S.H. et al., PNAS, 1998, vol. 95, pp. 8991-8996.
Wright J.M. et al., Physiol Genomics, 2004, vol. 16, No. 2, pp. 204-211.
Hazelmann A. et al., Pulmornary Pharmacology & Therapeutics, 2010, vol. 23, No. 4, pp. 235-256.
Al-Nakkash L. et al., Europ J Physiology, 1999, vol. 437, No. 4, pp. 553-561.
Schermuly et al, "Subthreshold Doses of Specific Phosphodiesterase Type 3 and 4 Inhibitors Enhance the Pulmonary Vasodilatory Response to Nebulized Prostacyclin with Improvement in Gas Exchange", The Journal of Pharmacology and Experimental Therapeutics, 2000, vol. 292(2), pp. 512-520.

* cited by examiner

COMPOSITION FOR THE TREATMENT OF CYSTIC FIBROSIS

CROSS-REFERENCE TO RELATED APPLICATIONS

This application is the U.S. national stage of International Patent Application No. PCT/EP2012/051880, filed on Feb. 3, 2012 and entitled NOVEL COMPOSITION FOR THE TREATMENT OF CYSTIC FIBROSIS, which claims the benefit of priority under 35 U.S.C. §119 from European Patent Application No. 11153541.5, filed on Feb. 7, 2011. The disclosures of the foregoing applications are incorporated herein by reference in their entirety.

FIELD OF THE INVENTION

The present invention provides compositions comprising a prostacyclin or prostacyclin analogue in combination with a phosphodiesterase inhibitor 4 for use in preventing or treating cystic fibrosis as well as specific compositions.

Prostaglandin I2 (prostacyclin; epoprostenol, PGI2) is an oxygenated metabolite of arachidonic acid formed enzymatically by the sequential activities of cyclooxygenase and PGI synthase enzymes. It is produced constitutively by vascular endothelial and smooth muscle cells and is induced under inflammatory conditions in vascular cells and macrophages.

PGI2 is a potent vasodilator and antithrombotic agent whose effects result from binding to a unique heptahelical G protein-coupled receptor termed the I prostanoid (IP)4 receptor. This receptor is coupled to $G_s$- and activates adenylate cyclase, resulting in an acute burst of intracellular cAMP. Since expression of CFTR and mutated CFTR is cAMP-dependent, substances which enhance intracellular levels of cAMP are of interest for development of drugs for treatment of CF. Most of these substances, such as forskolin, however, induce a rather unspecific elevation of cAMP, which may have also very harmful effects such as inflammation. Thus there is an unmet need of specific enhancers of cAMP in lung epithelial cells.

Treprostinil is a potent IP receptor agonist, although its specificity for this receptor is unknown. Sprague R. S. et al., Microcirculation 2008 July; 15(5):461-71, showed that Prostacyclin analogues (UT-15, Remodulin) stimulate receptor-mediated cAMP synthesis and ATP release from rabbit and human erythrocytes.

Nucleic phosphodiesterase (PDE) is an enzyme that catalyzes the hydrolysis of cAMP and cyclic 3",5-guanosine monophosphate (cGMP) to inactive 5"-nucleotide products. cAMP and cGMP exhibit many intracellular effects, mediated largely through their stimulatory effect on multisubstrate protein kinases. By inhibiting PDE, the level of cAMP and cGMP is increased, resulting in relaxation of airway smooth muscle and inhibition of inflammatory cell activation. PDE4, PDE7 and PDE8 are specific for cAMP.

Phosphodiesterase inhibitors block one or more of the subtypes of the enzyme phosphodiesterase (PDE), therefore preventing the inactivation of the intracellular second messengers cyclic adenosine monophosphate (cAMP) and cyclic guanosine monophosphate (cGMP) by the respective PDE subtype(s). Isozymes of cyclic-3', 5'-nucleotide PDE are a critically important component of the cAMP protein kinase A (PKA) signaling pathway. Eleven PDE families have been identified. The superfamily of PDE isozymes consists of at least nine gene families (types), PDE1 to PDE11. Some PDE families are very diverse and consist of several subtypes and numerous isoform-splice variants.

Examples for unspecific PDE inhibitors are theophylline and related xanthine compounds, caffeine, aminophylline etc. Vinpocetine is a PDE1 selective inhibitor. Known PDE2 selective inhibitors are EHNA or Anagrelide, PDE3 selective inhibitors are Enoximone or Milrinone.

PDE4 is the major cAMP-metabolizing enzyme found in inflammatory and immune cells. PDE4 inhibitors have proven potential as anti-inflammatory drugs, especially in inflammatory pulmonary diseases such as asthma, COPD, and rhinitis. They suppress the release of cytokines and other inflammatory signals, and inhibit the production of reactive oxygen species. Known PDE4 inhibitors are for example Mesembrine, Rolipram, Ibudilast etc.

PDE5 inhibitors are primarily metabolized by the cytochrome P450 enzyme CYP3A4. The potential exists for adverse drug interactions with other drugs which inhibit or induce CYP3A4, including HIV protease inhibitors, ketoconazole, itraconazole, and other anti-hypertensive drugs such as Nitro-spray. Examples of PDE5 inhibitors are Sildenafil, Tadalafil, Verdenafil or Udenafil.

Cystic fibrosis (CF) is a genetic disease resulting from mutations in a 230 kb gene on chromosome 7 encoding a 1480 amino acid polypeptide known as the cystic fibrosis transmembrane conductance regulator (CFTR) which serves as a chloride channel in epithelial membranes. Over 1000 mutant alleles have been identified to date. The most common mutation, ΔF508, is the deletion of a phenylalanine residue at codon 508 in the cystic fibrosis transmembrane conductance regulator (CFTR) protein. This mutation results in a severe reduction in CFTR function, and leads to the classic cystic fibrosis phenotype characterized with abnormality in exocrine gland functions like raised sweat chloride, recurrent respiratory infection with bronchiectasis, and early-onset of pancreatic insufficiency.

Clinically, CF is usually suspected when one or more typical CF phenotypic features are present in a subject. This could be a chronic pulmonary disease alone or very often associated with gastrointestinal and nutritional abnormalities (e.g. pancreatic insufficiency and recurrent pancreatitis), salt loss syndromes and male urogenital abnormalities (i.e. obstructive azoospermia). In the human lung, thick, tenacious secretions obstruct the distal airways and submucosal glands, which express CFTR. Ductular dilatation of these glands (associated with blockage by mucus) and the plastering of airway surfaces by thick, viscous, neutrophil dominated mucopurulent debris are among the pathological hallmarks of the disease. Pulmonary inflammation is another major cause of the decline in respiratory function in subjects with cystic fibrosis and may precede the onset of chronic infection. Mucinous impaction and thick concretions within pancreatic ducts lead to chronic fibrosis, fatty replacement of the gland, or both in a large subgroup of subjects with a previous diagnosis of idiopathic or alcoholic pancreatitis.

Cystic fibrosis is the most common fatal inherited disease in the Caucasian population, affecting about 4 in 10,000 children. In the United States, the median age at death has increased from 8.4 years of age in 1969 to 14.3 years of age in 1998. The mean age of death has increased from 14 years in 1969 to 32.4 years of age in 2003 (Cystic Fibrosis Foundation). For children born in the 1990s, the median survival is predicted to be over 40 years. A major contributor to the significant increase in life expectancy is improved treatment of chronic respiratory tract infections and elimination of mucus in CF subjects as well as improved nutrition and earlier diagnosis.

Loss of the cystic fibrosis transmembrane conductance regulator (CFTR) anion conductance from the apical membranes of airway epithelia disrupts regulation of the airway surface liquid layer. This leads to impaired mucociliary clearance, airway infection, and inflammation characteristic of cystic fibrosis (CF). The common ΔF508 mutation of CFTR is present on at least one allele in >90% of CF patients, and >50% of patients are homozygous for ΔF508, the rest being compound heterozygous. A central issue in CF disease is the inability of this common CFTR variant to achieve the native, folded state that will exit from the endoplasmic reticulum (ER) and traffic to the epithelial cell apical membrane.

If acquisition of the native conformation is retarded, CFTR is thought to maintain excessive or prolonged interactions with molecular chaperones, which then target the protein for degradation by mechanisms that police the ER for misfolded or incompletely complexed proteins. ER-associated degradation (ERAD) involves ubiquitination of aberrant proteins and their delivery to the proteasome for digestion. If ERAD lags behind the rate of protein synthesis, or during treatment with proteasome inhibitors, aggregates of the mutant protein accumulate. CFTR was the first integral membrane mammalian protein to be identified as a substrate for ubiquitin-proteasome mediated degradation, and it has served as a model for the growing list of diseases of protein conformation, which account for a diverse set of pathological etiologies.

Essentially all of the ΔF508 CFTR produced by the cell is destroyed by ERAD. Also, due to its complex folding pattern, 60-70% of the wild-type (wt) protein may be similarly degraded, although this may vary among cell types. The proteolytic cleavage patterns of the immature forms of wt and ΔF508 CFTR are similar, whereas the digestion pattern of mature wt CFTR is different. This finding supports the concept that at least a portion of the ER-retained mutant CFTR is present in an intermediate conformation that is formed along the normal CFTR folding pathway, as opposed to the formation of a variant protein structure. For ΔF508 CFTR, this intermediate conformation cannot proceed beyond a critical step in the folding process, but this implies that ΔF508 CFTR could be rescued if it were possible to facilitate this step.

A variety of experimental conditions, such as reduced temperature, incubation with chemical chaperones, or pharmacological correctors, can promote the escape of ΔF508 CFTR from the ER, yielding a functional anion channel at the cell surface. In addition, investigators have reported restoration of ΔF508 CFTR function by coexpression of various partial CFTR constructs or subdomains from wt CFTR. However, a consensus as to which CFTR subdomains are effective in mutant protein rescue is not apparent, and the mechanism of this effect remains obscure. In addition, CFTR fragment-induced rescue has been observed primarily in cells exogenously overexpressing both the CFTR fragment and full-length ΔF508 CFTR.

WO 08/098,196 describes the treatment of pulmonary fibrosis using Treprostinil. Pulmonary fibrosis, however, is an interstitial lung disease that is caused by the accumulation of collagen fibres in the lung; this restricts the capacity of the lung to inhale air: the lung loses its compliance and the airway resistance increases (compliance=1/resistance). As the disease progresses there is also an increase in vascular resistance. The site of action of Treprostinil in pulmonary fibrosis is the vasculature and the interstitial space in the alveola.

Tissieres et al. describe studies using Iloprost for the treatment of a patient with cystic fibrosis and secondary pulmonary hypertension. It is disclosed that aerolised Iloprost was effective in lowering pulmonary artery pressure (The annals of thoracic surgery, vol, 78, no. 3, E48-E50).

US2001/006979 A1 describes the use of prostacyclin derivatives like Iloprost or Cicaprost for the treatment of fibrotic diseases.

Cystic fibrosis is unrelated to pulmonary fibrosis because it is a disease that originates in the bronchial epithelium. Because of the absence of CFTR, there is too little water in the mucus that covers the bronchial epithelium; accordingly, the cilia cannot move the thick mucus and mucociliary clearance breaks down (mucociliary clearance works like a conveyor belt, where the cilia beat rhythmically in a concentrated manner to move the mucus back to the trachea and pharynx, from where it may be cleared by swallowing or coughing etc.). If mucociliary breaks down, the bacteria cannot be removed from the bronchi, the bronchi are colonized by bacteria and there are repeated bouts of lung infections that destroy the lung. The situation can be remedied by restoring Cl-fluxes to the bronchial epithelium. Thus, in cystic fibrosis the site of action is the airway epithelium of the bronchi. The site of action is anatomically distinct (lung interstitium vs. bronchial airway), involves a different set of cells (fibroblasts, vascular smooth muscle cells, endothelium versus absorbing and secreting bronchial epithelial cells) and presumably also involves different receptors (prostacyclin receptor vs possibly EP2-receptor).

DE102005016345A1 and US2005101608A1 describe the use of PDE5 inhibitors for the treatment of pulmonary hypertension.

US2009325976A1 discloses new prostacyclin derivatives which may be used also in combination with a PDE 5 inhibitor for use in the treatment of pulmonary arterial hypertension.

Clinically used PDE inhibitors were tested for activating the chloride secretion in the setting of low cAMP levels as described by Cobb B. R. et al., (Am J Respir Cell Mol. Biol. 2003 September; 29(3 Pt 1):410-418).

PDE 5 inhibitors, Sildenafil and Vardenafil, and their role in chloride transport in cystic fibrosis are described by Lubamba B. Et al. (Am J Respir Crit. Care Med. 2008 Mar. 1; 177(5):506-515).

PDE 5 inhibitors and their role in ΔF508 CFTR channel function is described by Clarke Lane L. (J Respir Crit. Care Med. 2008 Mar. 1; 177(5):469-70).

In WO2010106494A1 the use of mesembrine HCl, a known weak PDE4 inhibitor for treating disorders is disclosed.

US20070249668 describes a composition containing a PDE inhibitor and a prostacyclin analogue to increase the ATP content in red blood cells.

Presently, no treatments of cystic fibrosis are available that significantly improve quality of life of patients over a longer period. Therefore it is an object of the invention to provide compositions for treatment that can enhance the expression of ΔF508 CFTR and/or chloride channel function in epithelial cells of the lung.

Short Description of the Invention

The object of the invention is achieved by providing a composition comprising at least one prostacyclin or an analogue, a derivative or a pharmaceutically acceptable salt thereof in combination with at least one PDE 4 inhibitor for use in preventing or treating cystic fibrosis. As an alternative embodiment, said composition can further comprise at least one PDE5 and/or PD7 and/or PDE8 inhibitor.

Specifically, the prostacyclin analogue is selected from the group of Treprostinil, Iloprost, Cicaprost or Beraprost or derivatives or pharmaceutically acceptable salts thereof. In one embodiment of the present invention the Treprostinil derivative is an acid derivative, a prodrug, a polymorph or an isomer of Treprostinil.

According to the invention, the PDE4 inhibitor can be specifically selected from the group of Ro 20-1724, Ibudilast, Roflumilast and its N-Oxide, Cilomilast, BAY 19-8004, CC3, AWD 12-281, SCH 351591, Ciclamilast, Piclamilast, CGH2466, Mesembrine, Rolipram, Luteolin and Drotaverine.

According to the invention, the PDE5 inhibitor can be specifically selected from Avanafil, Lodenafil, Mirodenafil, Sildenafil citrate, Tadalafil, Vardenafil and Udenafil; the PDE7 and PDE8 inhibitors may be selected from Dipyridamol, BRL-50481 and PF-04957325

According to a specific embodiment of the invention, the composition specifically consists of one type of prostacyclin analogue and one type of PDE4 inhibitor.

As a specific embodiment, the composition comprises Treprostinil and a PDE4 inhibitor selected from the group of RO 20-1724, Roflumilast and Ibudilast.

A further embodiment of the invention, the composition comprises additional PDE inhibitors selected from PDE5, PDE7 or PDE8 inhibitors.

In another embodiment, the invention provides a composition free of interferon.

Specifically, the inventive composition is formulated as a pharmaceutical composition.

Any known administration forms can be used for administering the inventive combination, for example it can be intravenous or subcutaneous administration or inhalation administration, or in an orally available form selected from the group of sustained release forms, tablets and capsules.

According to a specific embodiment, the effective amount of Treprostinil or a pharmaceutically acceptable salt thereof is preferably of about 1.0 ng/kg of body weight, Ibudilast is preferably up to 5×30 mg, preferably up to 2×30 mg the effective amount of the PDE4 inhibitor is approx. 0.5 mg. Additionally, one or more inhibitors of the group of PDE5 and PDE7 inhibitors may be contained in an effective amount of about 0.5 mg of each of the inhibitors.

The present invention also provides an in vitro method for increasing the cAMP level in a cell wherein said cell is contacted with at least one prostacyclin or prostacyclin analogue and at least one PDE4 inhibitor or a pharmaceutically acceptable salt thereof. Additionally, a PDE5, PDE7 and/or PDE8 inhibitor may further be used according to said method.

Specifically, the cell is an epithelial cell, more specifically it may be a bronchoepithelial cell.

A therapeutic combination is also provided, comprising at least one prostacyclin or prostacyclin analogue and at least one PDE4 inhibitor or a pharmaceutically acceptable salt thereof, wherein the prostacyclin analogue and the PDE4 inhibitor are provided in amounts which together are sufficient to treat and/or prevent at least one symptom associated with cystic fibrosis. More specifically, the prostacyclin analogue and PDE4 inhibitor are formulated for administration by inhalation.

Said therapeutic composition may, according to an alternative embodiment, contain at least one further inhibitor selected from the group of PDE5, PDE7 and PDE8 inhibitors.

FIGURES

FIG. 1: Accumulation of cAMP in IB3-1 cells after incubation with Treprostinil alone or in combination with the PDE 4 inhibitors Ibudilast (100 µM) and Cilostazol (100 µM).

Figure 2:
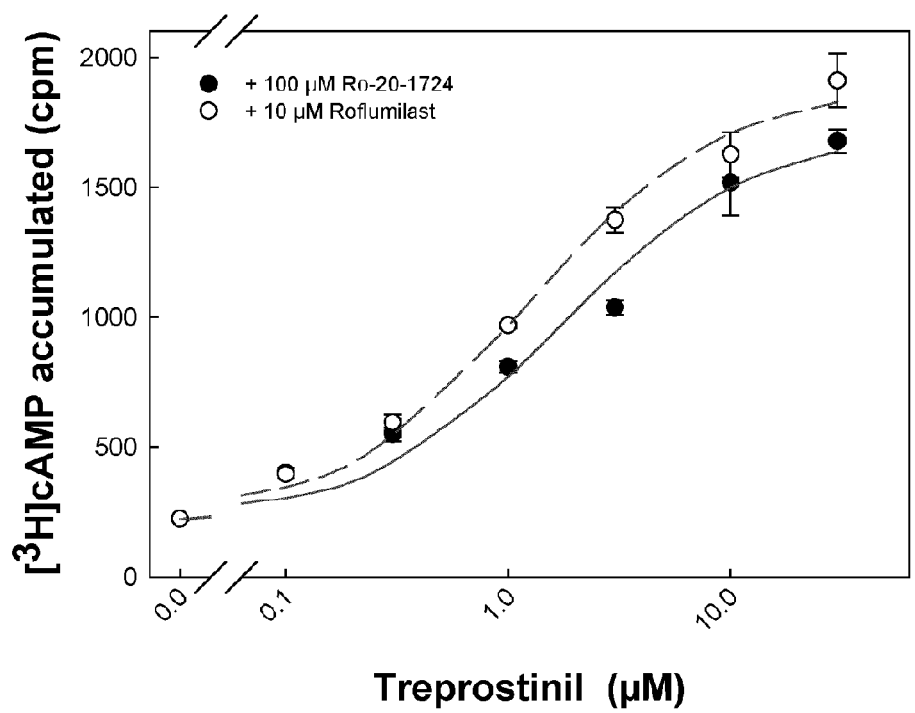

FIG. 2: Accumulation of cAMP in IB3-1 cells after incubation with Treprostinil in combination with the PDE 4 inhibitors RO-20-1724 (100 µM) and Roflumilast (10 µM).

Figure 3:
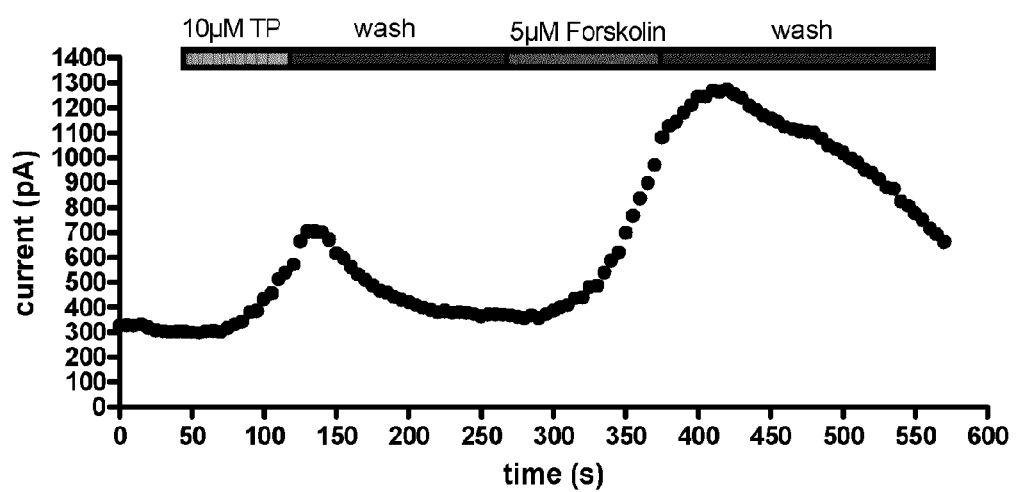

FIG. 3: Activation of a Cl-current by Treprostinil in the human bronchial epithelial IB3-1 cell line transiently expressing CFTR-wt.

Figure 4:
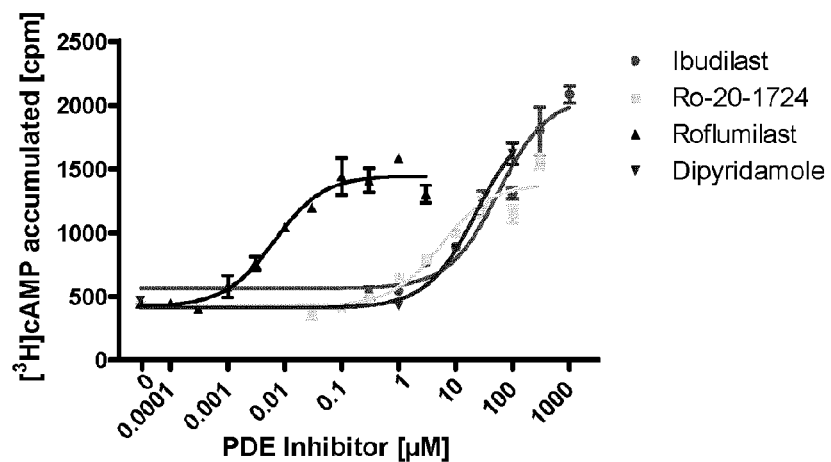

FIG. 4: Accumulation of cAMP in IB3-1 cells stimulated by 10 µM Treprostinil in the absence and presence of the indicated concentrations of Dipyridamole, Ibudilast, RO20-1724 or Roflumilast. Cells were metabolically prelabelled with [$^3$H]adenine for 4 h and subsequently incubated with the indicated compounds for 30 min. The formation of [$^3$H]cAMP was determined as outlined under Materials and Methods. Data are means±s.e.m. (n=3).

Figure 5:
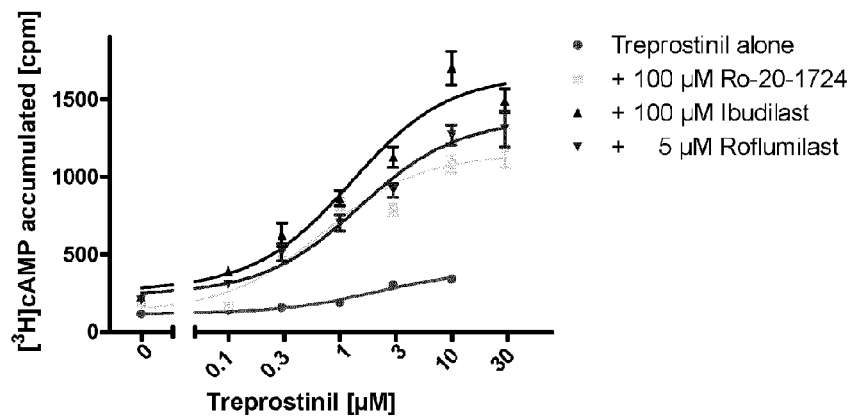

FIG. 5: Concentration-response curve for Trepostinil-induced cAMP accumulation in IB3-1 cells. Cells were incubated with increasing concentrations of Treprostinil in the absence and presence of the indicated concentrations of Ibudilast, RO20-1724 or Roflumilast. Cells were metabolically prelabelled with [$^3$H]adenine for 4 h and subsequently incubated with the indicated compounds for 30 min. The formation of [$^3$H]cAMP was determined as outlined under Materials and Methods. Data are means±s.e.m. (n=3).

Figure 6:
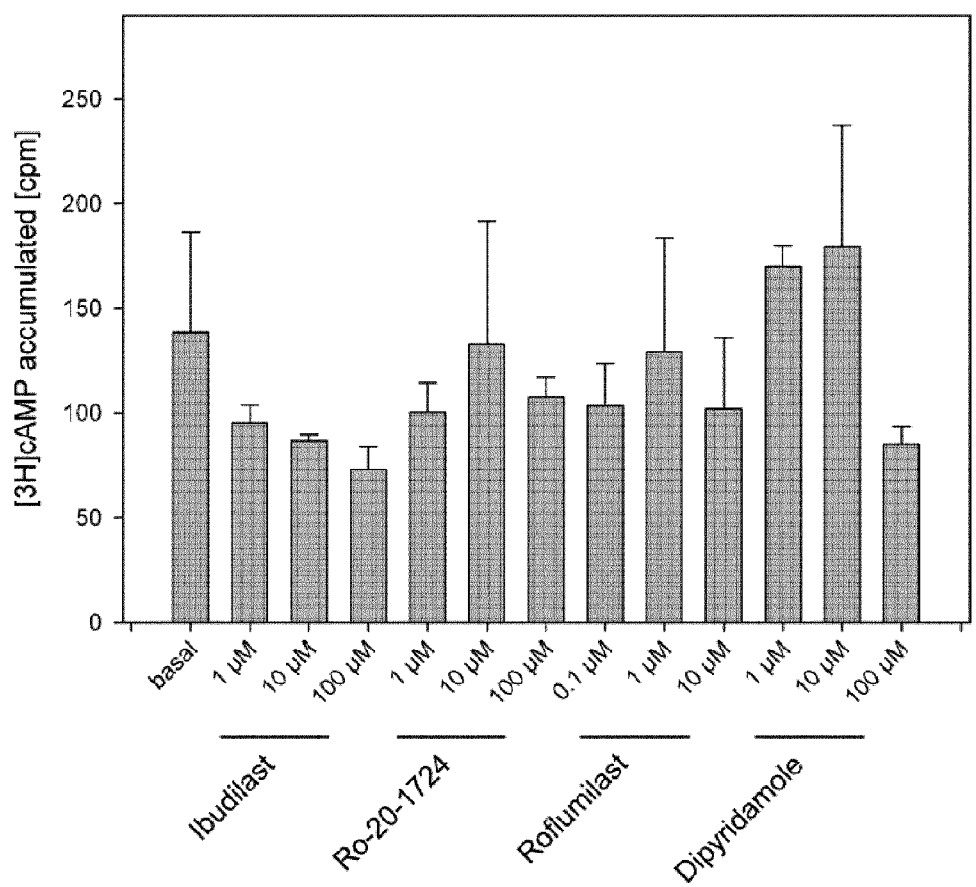

FIG. 6: Effect of selected phosphodiesterase inhibitors on basal cAMP accumulation in IB3-1 cells. Cells were metabolically prelabelled with [$^3$H]adenine for 4 h and subsequently incubated in the absence (basal) and presence of the indicated concentrations of Dipyridamole, Ro-20-1724 or Roflumilast for 30 min. The levels of [$^3$H]cAMP were determined as outlined under Materials and Methods. Data are means±s.e.m. (n=3).

DETAILED DESCRIPTION OF THE INVENTION

It has been surprisingly found by the inventors that prostacyclin or analogues or a pharmaceutically acceptable salt thereof in combination with a PDE4 inhibitor can be used for treating cystic fibrosis. It was shown that a combination of prostacyclin or prostacyclin analogues and PDE4 inhibitors have synergistic effect in cAMP increase, specifically in the affected human airway epithelial cells, compared to the use of single substances. Said effect may further be enhanced by the presence of further PDE inhibitors selected from PDE5, PDE7 and PDE8 inhibitors.

Synthetic prostacyclin analogues can be for example, but are not limited to, Treprostinil, Iloprost, Cicaprost or Beraprost.

Treprostinil is marketed as Remodulin™. Treprostinil is a (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid monosodium salt.

Iloprost is marketed as "Ilomedine" and is a 5-{(E)-(1S,5S,6R,7R)-7-hydroxy-6-[(E)-(3S,4RS)-3-hydroxy-4-methyl-1-octen-6-inyl]-bi-cyclo[3.3.0]octan-3-ylidene}pentanoic acid.

Beraprost is a 2,3,3a,8b-tetrahydro-2-hydroxy-1-(3-hydroxy-4-methyl-1-octen-6-ynyl)-1H-cyclopenta(b)benzofuran-5-butanoic acid.

Cicaprost is a 2-[(2E)-2-[(3aS,4S,5R,6aS)-5-hydroxy-4-[(3S,4S)-3-hydroxy-4-methylnona-1,6-diynyl]-3,3a,4,5,6,6a-hexahydro-1H-pentalen-2-ylidene]ethoxy]acetic acid.

In reference to prostacyclin, PDE4 and PDE5, PDE7 or PDE8 inhibitors, according to the present invention, the term "prostacyclin analogues", "inhibitor analogs" or "PDE4, PDE5, PDE 7 or PDE8 inhibitor analogs" means derivatives or analogues of said substances. The terms "analogue" or "derivative" relate to a chemical molecule that is similar to another chemical substance in structure and function, often differing structurally by a single element or group, which may differ by modification of more than one group (e.g., 2, 3, or 4 groups) if it retains the same function as the parental chemical substance. Such modifications are routine to skilled persons, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Derivatives can also include conjugates, such as biotin or avidin moieties, enzymes such as horseradish peroxidase and the like, and radio-labeled, bioluminescent, chemoluminescent, or fluorescent moieties. Further, moieties can be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.). The term "derivative" also includes within its scope alterations that have been made to a parent sequence including additions, deletions, and/or substitutions that provide for functionally equivalent or functionally improved molecules.

Suitable prostacyclin or prostacyclin analogue derivatives include but are not limited to acid derivatives, pro-drugs, sustained release forms, inhaled forms and oral forms of Treprostinil, Iloprost, Cicaprost or Beraprost.

According to a specific embodiment of the invention, the Treprostinil derivative is selected from the group of acid derivatives, prodrugs, polymorphs or isomers of Treprostinil.

Similarly, Iloprost, Cicaprost or Beraprost derivatives can be acid derivatives, prodrugs, polymorphs or isomers therefrom. The term prostacyclin derivative also covers pharmaceutically acceptable salts thereof. A pharmaceutically acceptable salt of a prostacyclin or a prostacyclin analogue of this invention can be formed between an acidic and a basic group of the compound, such as an amino functional group, or a base and an acidic group of the compound, such as a carboxyl functional group.

Specifically, physiologically acceptable salts of prostacyclin analogues include salts derived from bases. Base salts include ammonium salts (such as quaternary ammonium salts), alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Specifically, the use of Treprostinil is advantageous according to the invention. Treprostinil can successfully enhance the expression of ΔF508 CFTR and/or the chloride channel function in epithelial cells of the lung of cystic fibrosis patients.

It has been surprisingly shown that a prostacyclin analogue in combination with a PDE4 inhibitor and optionally in combination with a PDE5 and/or PDE7 and/or PDE8 inhibitor leads to synergistic stimulation of cAMP production and/or increase of cAMP content in bronchoepithelial cells.

Interestingly PDE3 inhibitors like Anagrelide and Cilostazol did not induce any accumulation of cAMP in experiments.

Given this ability to stimulate cAMP production through the IP receptor, and the limited presence of IP receptors to a small number of cell-types (such as epithelial lung cells), a prostacyclin or analogue thereof, for example Treprostinil might induce expression and gating of CFTR and mutCFTR in a specific manner which can be used for treatment of CF, in particular, when combined with said PDE4 inhibitors to induce a long lasting increase in cAMP levels within the airway epithelium.

According to a further embodiment, said cAMP increase may further be induced by combination of a PDE4 inhibitor with further selected PDE inhibitors from the group of PDE5, PDE7 and/or PDE8 inhibitors.

PDE4 inhibitors are approved for the treatment of COPD and asthma; the main target in COPD and asthma is to reduce the hyperreactivity of the smooth muscle cells lining the airways. Raising cAMP levels in smooth muscle cells has long been known to cause relaxation of the smooth muscle, via action on myosin light chain kinase. In addition, PDE4 inhibitors are thought to reduce the immune response that drives allergic asthma by targeting monocytes, eosinophil and basophil granulocytes, B and T cells, e.g. the inflammatory cells. Neither of these two mechanisms is relevant as a mode of action in cystic fibrosis. In cystic fibrosis, cAMP levels must be raised in a very different cellular compartment, i.e. the airway epithelium. In fact, to the best of our knowledge, there are no scientific reports that show that PDE4 is the relevant isoform that enhances receptor-mediated cAMP accumulation within the airway epithelium.

According to the present invention, any PDE4 inhibitor or its analogue can be used having inhibitory activity towards the PDE4 enzyme. Thus, it is not excluded that the PDE4 inhibitor can further inhibit other PDE enzymes as well.

Specifically, the PDE4 inhibitor can be a specific PDE4 inhibitor.

The PDE4 inhibitor of the invention can be, but is not limited to Ro 20-1724, Ibudilast, Roflumilast (3-(cyclopropylmethoxy)-N-(3,5-dichloropyridin-4-yl)-4-(difluoromethoxy)benzamide) and its N-Oxide, Cilomilast, BAY 19-8004, CC3, AWD 12-281 (N-(3,5-dichloro-4-pyridinyl)-2-[1-(4-fluorobenzyl)-5-hydroxy-1H-indol-3-yl]-2-oxoacetamide), SCH 351591 (N-(3,5-dichloro-1-oxido-4-pyridinyl)-8-methoxy-2-(trifluoromethyl)-5-quinoline carboxamide), Ciclamilast, Piclamilast, CGH2466, Mesembrine, Rolipram, Luteolin and Drotaverine or functional analogs thereof.

More specifically, the composition for use of preventing or treating CF, specifically by raising the cAMP levels in the bronchoepithelial cells of individuals suffering from CF can specifically comprise Treprostinil and Roflumilast or Treprostinil and Ibudilast or Treprostinil and Ro-20-1724. PDE5 inhibitors have been shown to increase cyclic nucleotide second messenger levels in the smooth muscle cells.

According to the present invention, any PDE5 inhibitor or its analogue can be used having inhibitory activity towards the PDE5 enzyme. Thus, it is not excluded that the PDE5 inhibitor can further inhibit other PDE enzymes as well.

According to the invention, the PDE5 inhibitor can be specifically selected from Avanafil (4-[(3-chloro-4-methoxybenzyl)amino]-2-[2-(hydroxymethyl)-1-pyrrolidinyl]-N-(2-pyrimidinylmethyl)-5-pyrimidinecarboxamide), Lodenafil (bis-(2-{4-[4-ethoxy-3-(1-methyl-7-oxo-3-propyl-6,7-dihydro-1H-pyrazolo[4,3-d]pyrimidin-5-yl)-benzenesulfonyl]piperazin-1-yl}-ethyl)carbonate), Mirodenafil (5-ethyl-3,5-dihydro-2-[5-([4-(2-hydroxyethyl)-1-piperazinyl]sulfonyl)-2-propoxyphenyl]-7-propyl-4H-pyrrolo[3,2-d]pyrimidin-4-one), Sildenafil citrate (1-[4-ethoxy-3-(6,7-dihydro-1-methyl-7-oxo-3-propyl-1H-pyrazolo[4,3-d]pyrimidin-5-yl) phenylsulfonyl]-4-methylpiperazine), Tadalafil (6R-trans)-6-(1,3-benzodioxol-5-yl)-2,3,6,7,12,12a-hexahydro-2-methyl-pyrazino[1', 2':1,6]pyrido[3,4-b]indole-1,4-dione), Vardenafil (4-[2-ethoxy-5-(4-ethylpiperazin-1-yl)sulfonyl-phenyl]-9-methyl-7-propyl-3,5,6,8-tetrazabicyclo[4.3.0]nona-3,7,9-trien-2-one) or Udenafil (3-(1-methyl-7-oxo-3-propyl-4,7-dihydro-1H-pyrazolo[4,3-d]pyrimidin-5-yl)-N-[2-(1-methylpyrrolidin-2-yl)ethyl]-4-propoxybenzenesulfonamide) or any functional analogs thereof.

In a specific embodiment of the invention, the composition may comprise Treprostinil, Roflumilast and optionally a PDE5, PDE7 or PDE8 inhibitor or Treprostinil, Ibudilast and optionally PDE5, PDE7 or PDE8 inhibitor or Treprostinil, Ro-20-1724 and optionally PDE5, PDE7 or PDE8 inhibitor.

In a further embodiment of the invention, the composition may comprise Beraprost, Roflumilast and optionally a PDE5, PDE7 or PDE8 inhibitor or Beraprost, Ibudilast and optionally a PDE5, PDE7 or PDE8 inhibitor or Beraprost, Ro-20-1724 and optionally a PDE5, PDE7 or PDE8 inhibitor.

In a further embodiment of the invention, the composition may comprise Iloprost, Roflumilast and optionally a PDE5, PDE7 or PDE8 inhibitor or Iloprost, Ibudilast and optionally a PDE5, PDE7 or PDE8 inhibitor or Iloprost, Ro-20-1724 and optionally a PDE5, PDE7 or PDE8 inhibitor.

In a further embodiment of the invention, the composition may comprise Cicaprost, Roflumilast and optionally a PDE5, PDE7 or PDE8 inhibitor or Cicaprost, Ibudilast and optionally a PDE5, PDE7 or PDE8 inhibitor or Cicaprost, Ro-20-1724 and optionally a PDE5, PDE7 or PDE8 inhibitor.

According to the present invention, any PDE7 or PDE8 inhibitor or its analogue may be used having inhibitory activity towards the PDE7 or PDE8 enzyme. Thus, it is not excluded that the PDE7 or PDE8 inhibitor can further inhibit other PDE enzymes as well.

According to the invention, the PDE7 inhibitor can be specifically selected from Dipyridamol and BRL 50481.

According to the invention, the PDE8 inhibitor can be specifically selected from 1,5-substituted nipecotic amides and PF-4957325.

In an alternative embodiment of the invention, the composition may specifically comprise Treprostinil, Roflumilast and Dipyridamol or Treprostinil, Ibudilast and Dipyridamol or Treprostinil, Ro-20-1724 and Dipyridamol.

In a further alternative embodiment of the invention, the composition may specifically comprise Beraprost, Roflumilast and Dipyridamol or Beraprost, Ibudilast and Dipyridamol or Beraprost, Ro-20-1724 and Dipyridamol.

In yet a further alternative embodiment of the invention, the composition may specifically comprise Iloprost, Roflumilast and Dipyridamol or Iloprost, Ibudilast and Dipyridamol or Iloprost, Ro-20-1724 and Dipyridamol.

In an further embodiment of the invention, the composition may specifically comprise Cicaprost, Roflumilast and Dipyridamol or Cicaprost, Ibudilast and Dipyridamol or Cicaprost, Ro-20-1724 and Dipyridamol.

Alternatively the composition may comprise Treprostinil, Roflumilast and BRL 50481 or Treprostinil, Ibudilast and BRL 50481 or Treprostinil, Ro-20-1724 and BRL 50481.

Alternatively, the composition may specifically comprise Treprostinil, Roflumilast and PF-4957325 or Treprostinil, Ibudilast and PF-4957325 or Treprostinil, Ro-20-1724 and PF-4957325.

According to the invention the term "at least one" or "a" means that one type of prostacyclin or prostacyclin analogue and one type of PDE4 inhibitor and optionally one or more of PDE5, PDE7 or PDE8 inhibitors is present for use in the treatment or prevention of cystic fibrosis, specifically for the use to increase the cAMP level in bronchoepithelial cells. However, alternatively, the composition may also comprise more than one type of prostacyclin or prostacyclin analogue and more than one type of PDE4 inhibitor and optionally one or more of PDE5, PDE7 or PDE8 inhibitors, specifically two, three, four or more than four types or any combinations of prostacyclins or prostacyclin analogues and PDE4 and optionally PDE5, PDE7 and/or PDE8 inhibitors.

The invention further provides a specific composition comprising Treprostinil and one or more PDE4 inhibitors selected from the group of RO 20-1724, Roflumilast and Ibudilast.

The inventive composition can be formulated as a pharmaceutical composition.

The composition of the invention can be present in any form which can be used for administration.

The specific dose of a compound administered according to this invention to obtain therapeutic or prophylactic effects will, of course, be determined by the particular circumstances surrounding the case, including, for example, the route of administration, the age, weight and response of the individual patient, the condition being treated and the severity of the patient's symptoms.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

The composition can be provided in a variety of systemic and topical formulations. The systemic or topical formulations of the invention are selected from the group of oral, intrabuccal, intrapulmonary, rectal, intrauterine, intradermal, topical, dermal, parenteral, intratumor, intracranial, intrapulmonary, buccal, sublingual, nasal, subcutaneous, intravascular, intrathecal, inhalable, respirable, intraarticular, intracavitary, implantable, transdermal, iontophoretic, intraocular, ophthalmic, vaginal, optical, intravenous, intramuscular, intraglandular, intraorgan, intralymphatic, slow release and enteric coating formulations. The actual preparation and compounding of these different formulations is known in the art and need not be detailed here. The composition may be administered once or several times a day.

Formulations suitable for respiratory, nasal, intrapulmonary, and inhalation administration are preferred, as are topical, oral and parenteral formulations. In general, the formulations are prepared by uniformly and intimately bringing the active compound into association with a liquid carrier, a finely divided solid carrier, or both, and then, if necessary, shaping the product into desired formulations.

Compositions suitable for oral administration may be presented in discrete units, such as capsules, cachets, lozenges, or tablets, each containing the composition as a powder or granules; as a solution or a suspension in an aqueous or non-aqueous liquid; or as an oil-in-water or water-in-oil emulsion.

Compositions suitable for parenteral administration comprise sterile aqueous and non-aqueous injection solutions of the active compound, which preparations are preferably isotonic with the blood of the recipient. These preparations may contain anti-oxidants, buffers, bacteriostatic agents and solutes which render the compositions isotonic with the blood of the recipient. Aqueous and non-aqueous sterile suspensions may include suspending agents and thickening agents. The compositions may be presented in unit-dose or multi-dose containers, for example sealed ampoules and vials, and may be stored in a freeze-dried or lyophilized condition requiring only the addition of the sterile liquid carrier, for example, saline or water-for-injection immediately prior to use.

Nasal and instillable formulations comprise purified aqueous solutions of the active compound with preservative agents and isotonic agents. Such formulations are preferably adjusted to a pH and isotonic state compatible with the nasal mucous membranes.

The composition disclosed according to the invention may be administered into the respiratory system either by inhalation, respiration, nasal administration or intrapulmonary instillation (into the lungs) of a subject by any suitable means, and are preferably administered by generating an aerosol or spray comprised of powdered or liquid nasal, intrapulmonary, respirable or inhalable particles. The respirable or inhalable particles comprising the active compound are inhaled by the subject, e.g. by inhalation or by nasal administration or by instillation into the respiratory tract or the lung itself. The formulation may comprise respirable or inhalable liquid or solid particles of the active compound that, in accordance with the present invention, include respirable or inhalable particles of a size sufficiently small to pass through the mouth and larynx upon inhalation and continue into the bronchi and alveoli of the lungs. In general, particles ranging from about 0.05, about 0.1, about 0.5, about 1, about 2 to about 4, about 6, about 8, about 10 microns in diameter. More particularly, about 0.5 to less than about 5 µm in diameter, are respirable or inhalable. Particles of non-respirable size which are included in an aerosol or spray tend to deposit in the throat and be swallowed. The quantity of non-respirable particles in the aerosol is, thus, preferably minimized. For nasal administration or intrapulmonary instillation, a particle size in the range of about 8, about 10, about 20, about 25 to about 35, about 50, about 100, about 150, about 250, about 500 µm in diameter is preferred to ensure retention in the nasal cavity or for instillation and direct deposition into the lung. Liquid formulations may be squirted into the respiratory tract or nose and the lung, particularly when administered to newborns and infants.

Aerosols of liquid particles comprising the active compound may be produced by any suitable means, such as with a nebulizer. Nebulizers are commercially available devices which transform solutions or suspensions of the active ingredient into a therapeutic aerosol mist either by means of acceleration of a compressed gas, typically air or oxygen. Suitable compositions for use in nebulizer consist of the active ingredient in liquid carrier, the active ingredient comprising up to 40% w/w composition, but preferably less than 20% w/w carrier being typically water or a dilute aqueous alcoholic solution, preferably made isotonic with body fluids by the addition of, for example sodium chloride. Optional additives include preservatives if the composition is not prepared sterile, for example, methyl hydroxybenzoate, antioxidants, flavoring agents, volatile oils, buffering agents and surfactants. Aerosols of solid particles comprising the active compound may likewise be produced with any sold particulate medicament aerosol generator. Aerosol generators for administering solid particulate medicament, product particles which are respirable, as explained above, and generate a volume of aerosol containing a predetermined metered dose of a medicament at a rate suitable for human administration. Examples of such aerosol generators include metered dose inhalers and insufflators.

In one embodiment, the delivery device comprises a dry powder inhalator (DPI) that delivers single or multiple doses of the composition. The single dose inhalator may be provided as a disposable kit which is sterilely preloaded with enough formulation for one application. The inhalator may be provided as a pressurized inhalator, and the formulation in a piercable or openable capsule or cartridge. The kit may optionally also comprise in a separate container an agent such as other therapeutic compounds, excipients, surfactants (intended as therapeutic agents as well as formulation ingredients), antioxidants, flavoring and coloring agents, fillers, volatile oils, buffering agents, dispersants, surfactants, antioxidants, flavoring agents, bulking agents, propellants and preservatives, among other suitable additives for the different formulations.

Due to the high metabolic stability of some prostacyclin analogues like Treprostinil, or if provided as lipid based or pegylated forms of the prostacyclins or prostacyclin analogues, the substances can also be administered as depot medicaments.

PDE4, PDE5, PDE 7 and PDE8 inhibitors are also metabolically stable, therefore the combination of the prostacyclin or prostacyclin analogue and the PDE4 inhibitor optionally together with one or more of PDE5, PDE 7 or PDE8 inhibitors can also be formulated as depot medicaments.

Aerosolized delivery of the composition may result in a more homogeneous distribution of the agent in a lung, so that deep lung delivery is obtained. Thereby the dosage of application may be reduced due to the sustained presence of the agent at the site of action in the lung.

The composition can for example be given by a nebulizer. The advantage of the nebulizer method of delivery is that less of the substance reaches the systemic circulation. The composition can be given several times a day, for example five to 10 times a day, however due to the synergistic effect of the prostacyclin or prostacyclin analogue and the PDE4, optionally in combination with one or more of PDE5, PDE7 and/or PDE8 inhibitors, the dosing frequency may generally be reduced.

The composition can be administered with any pharmaceutically acceptable substances or carriers or excipients as known in the art. These can be for example, but are not restricted to water, neutralizing agents like NaOH, KOH, stabilizers, DMSO, saline, betaine, taurine etc.

The term "pharmaceutically acceptable" means approved by a regulatory agency of the Federal or a state government or listed in the U.S.

The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration.

The amount of the inventive composition can be selected by any skilled person, specifically the amount of the prostacyclins or prostacyclin analogues or pharmaceutically acceptable salts thereof, specifically the amount of Treprostinil is at least 1.0 ng/kg of body weight. The amount of PDE4 or PDE5 inhibitor can be easily selected by skilled persons, too. Specifically, the amount of PDE4 or PDE5 or PDE 7 or PDE8 inhibitor is about 0.5 mg for Roflumilast or about 30 mg Ibudilast, at least once per day, specifically at least two times/day.

The present invention additionally provides a method for increasing the cAMP level in a cell wherein said cell is contacted with at least one prostacyclin or prostacyclin analogue and at least one PDE4 and optionally at least one of PDE5, PD7 or PDE8 inhibitors. The increase of cAMP in said cells can be at least 10%, preferably at least 25%, preferably at last 50%, more preferred at least 100% compared to single treatment with a prostacyclin or a PDE4 and/or PDE5 or PDE7 or PDE8 inhibitor.

A therapeutic combination, comprising at least one prostacyclin analogue and at least one PDE4 and optionally at least one PDE5 and/or PDE7 inhibitor and/or PDE8 inhibitor, wherein the prostacyclin analogue and PDE4 and/or PDE5 inhibitor and/or PDE7 inhibitor and/or PDE8 inhibitor are provided in amounts which together are sufficient to treat and/or prevent at least one symptom associated with cystic fibrosis is provided, too. Specifically, an increase of the cAMP level in the epithelial cells of the lung of CF patients can be reached by administering the inventive therapeutic combination preparation. Specifically, at least one of the prostacyclin analogue and PDE4 and optionally one or more of PDE5, PDE7 or PDE8 inhibitors are formulated for administration by inhalation.

In a specific embodiment of the present invention, a combination therapy is disclosed for treating cystic fibrosis. According to a specific embodiment, the symptoms associated with reduced cAMP levels in bronchoepithelial cells of patients with CF can be treated or prevented by using the inventive combination therapy. Possibly, one or more additional agents can also be administered.

The prostacyclin or prostacyclin analogue and the PDE4 and optionally the PDE5, PDE7 or PDE8 inhibitor may be administered together, for example in a single tablet or capsule or inhalation formulation or the PDE4 and optionally other PDE inhibitors of the invention as well as optional additional agents may be administered separately from the prostacyclin or prostacyclin analogue.

The invention further provides a kit and its use for treating or preventing a condition associated with cystic fibrosis in a subject, comprising (i) an effective amount of a prostacyclin or prostacyclin analogue, (ii) a PDE4 inhibitor, specifically Roflumilast, Ro-20-1724 or Ibudilast, and optionally one or more compounds selected form the group of PDE5, PDE7 and PDE8 inhibitors, (iii) one or more pharmaceutically acceptable carriers and/or additives, and (iv) instructions for use in treating or preventing cystic fibrosis in a subject, preferably a human.

Said components (i) and (ii) and (iii) can be in a form suitable for intravenous administration, for inhalation or for oral administration.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

IB3-1 cells were plated on 6 well-plates (0.2*106 cells/well in FIG. 1; 0.4*10$^6$ cells in FIG. 2) in complete growth medium (LHC-8+5% FCS). The following day, the adenine nucleotide pool was metabolically labeled by incubation with [3H]adenine (1 µCi/well) in Dulbecco's Modified Eagle Medium (DMEM) containing adenosine deaminase (1 unit/ml) for 4 h. Thereafter the medium was replaced with fresh medium; the cells were stimulated by sole addition of Treprostinil (in logarithmically spaced concentrations ranging from 0.1 to 30 µM) or of Treprostinil in combination with the indicated concentrations of PDE-inhibitors. After an incubation of 30 min, the cells were lysed by the addition of perchloric acid.

The formation of [3H]cAMP was determined by sequential chromatography on Dowex 50WX-4 and neutral alumina columns followed by liquid scintillation counting of the eluate. The assay was performed in triplicate.

The results are shown in FIGS. 1 and 2. The difference between the maximum response in FIG. 1 and FIG. 2 is mainly due to the fact that the number of cells/well in FIG. 2 is about twice as high as that employed in FIG. 1.

Example 2

IB3-1 cells endogenously express only mutated CFTR-ΔF508, which is retained within the cells. Using appropriated manipulations (e.g., pharmacochaperones or low temperature incubations), it is possible to translocate the mutant CFTR-ΔF508 from the endoplasmic reticulum to the ER; when inserted at the cell surface, a Cl-conductance can be stimulated by elevating cAMP. The resulting Cl-conductance, however, is small. In order to unequivocally prove that the cAMP accumulation induced by Treprostinil translated into an activation of CFTR, we transiently expressed a GFP-tagged version of wild type CFTR (the GFP tag allowed for the identification of cells that expressed the protein at the cell surface). As can be seen from FIG. 3, Treprostinil caused a robust activation of the current induced by a depolarization from −40 mV holding potential to +60 mV. The maximum effect was delayed, i.e. it was only observed several seconds after wash-in of the compound. Likewise, there was also a hysteresis in the turn-off reaction; the current decayed to basal only ~100 s after washout. These delayed responses reflect the (i) intervening signaling cascade (i.e., the receptor-dependent activation of $G_s$, $Gα_s$-dependent activation of cAMP formation and the ensuing protein kinase A-dependent phosphorylation of CFTR) and (ii) the delayed deactivation of increased cAMP by phosphodiesterases. Similar delays were also seen, if cells were stimulated with forskolin, a direct activator a adenylyl cyclase, which was used as a positive control.

These observations prove that Treprostinil can activate CFTR in bronchial epithelial cells.

Methods:

Electrophysiology

The whole cell patch clamp technique was used for current recordings performed at 22±1.5° C. using an Axoclamp 200B patch clamp amplifier (Axon Instruments). Pipettes had resistances between 1 and 2 MΩ when filled with the recording pipette solution (composition: 110 mM CsCl, 5 mM EGTA, 2 mM $MgCl_2$, 1 mM $K_2$.ATP, 10 mM Hepes, pH adjusted to 7.2 with CsOH). Voltage-clamp protocols and data acquisition were performed with pclamp 6.0 software (Axon Instruments). Data were low-pass filtered at 2 kHz (−3 dB) and digitized at 10-20 kHz. Cells were continuously superfused with external solution (composition: 145 mM NaCl, 4.5 mM KCl, 2 mM $CaCl_2$, 1 mM $MgCl_2$, 5 mM glucose, 10 mM Hepes, pH adjusted to 7.4 with NaOH). When indicated, the external solution contained Treprostinil (10 µM) or forskolin (5 µM), switching between solutions was achieved by electronically controlled pressure valves.

Based on the results of example 1, a sustained response is expected, if Treprostinil is combined with PDE 4 or 5 inhibitors, e.g., 10 µM Roflumilast or 100 µM Ibudilast or 10-100 µM Tadalafil or Sildenafil or Vardenafil.

Cell Culture:

IB3-1 cells were grown on dishes (Nunc, 3.5 cm diameter) covered with fibronectin (10 µg/mL) rat collagen I (30 µg/mL) and BSA 10 µg/mL) in LHC-8 medium (Gibco) containing 5% fetal calf serum (FCS). Cells were transiently transfected with a plasmid driving the expression of human GFP-tagged wild type CFTR by using Lipofectamine Plus® (Invitrogen) according to the instructions of the manufacturer.

Representative current amplitudes recorded in the whole cell patch clamp configuration at +60 mV. A transiently transfected IB3-1 cell expressing GFP-tagged wild type CFTR was selected under fluorescent light and clamped to a holding potential at −40 mV. Depolarization was induced by a voltage step to +60 mV for 50 ms and the current amplitude was recorded. Wash-in of Treprostinil (10 µM final concentration, TP) was initiated at the time point 50 s and terminated at 125 s. Forskolin was washed in at 275 s and was removed at 375 s. Results are shown in FIG. 3.

Example 3

Introduction

Previous observations indicated that, in human airway epithelial cells, the Treprostinil-induced cAMP accumulation was specifically enhanced by inhibitors of phosphodiesterase-4 (PDE4) isoforms.

Materials and Methods

Cell Lines and Cell Culture:

The following human bronchial epithelial cell lines were obtained through ATCC: BEAS-2B (ATCC CRL-9609), NuLi-1 (ATCC CRL-4011), IB3-1 (ATCC CRL-2777), CuFi-1 (ATCC CRL-4013). Cells were propagated using the culture conditions outlined in the ATCC recommendations, e.g., I3B-1 cells were maintained on dishes coated with fibronectin (10 µg/m) rat collagen I (30 µg/ml) and BSA 10 µg/mL) in LHC-8 medium (Gibco) containing 5% fetal calf serum (FCS) at 37° C. in a 5% $CO_2$ humified atmosphere. BEAS-2B cells were maintained at 37° C. in a 5% CO2 humified atmosphere on dishes precoated with collagen IV (60 µg/ml in 0.25% acetic acid) in BEGM medium (Lonza); the GA-1000 (gentamycin-amphotericin B mix) provided with the BEGM kit was not added to the medium. The level of endogenous expression of CFTR was too low to obtain a reliable signal. Accordingly, BEAS-2B cells were transiently transfected with a plasmid driving the expression of human GFP-tagged wild type CFTR by using Lipofectamine Plus® (Invitrogen) according to the instructions of the manufacturer. Cells expressing this GFP-tagged CFTR were identified by fluorescence microscopy and subjected to patch clamp recordings as outlined below.

cAMP Accumulation Assay:

IB3-1 cells were seeded onto PDL-coated wells of 6-well plates (2 to 2.5*$10^5$ cells/well) in complete growth medium (LHC-8+5% FCS). On the following day, the cellular adenine nucleotide pool was metabolically labelled by incubation with [$^3$H]adenine (1 µCi/well) in Dulbecco's Modified Eagle Medium (DMEM) in the presence of adenosine deaminase (5 µg/ml) for 4 h. Subsequently, the medium was replaced with fresh DMEM and the formation of cAMP was stimulated by addition of 5 µM forskolin, a direct activator of the adenylyl cyclase, or 10 µM treprostinil in the absence and presence of different concentrations of the following phosphodiesterase (PDE) inhibitors: ibudilast (0.3-1000 µM), Ro-20-1724 (0.03-300 µM), roflumilast (1 nM-10 µM), dipyridamole (0.01-100 µM), aminone (1, 10, 100 µM), anagrelide (1, 10, 100 µM), enoximone (1, 10, 100 µM), milrinone (1, 10, 100 µM) and cilostazol (0.1 to 100 µM) for 20 min at 37° C. In some instances, the effect of these inhibitors on basal cAMP accumulation was examined by incubating cells in the absence of any additional stimulus with increasing concentrations of PDE-inhibitors (i.e., dipyridamole, ibudilast and Ro-20-1724 at 1, 10 and 100 µM; roflumilast at 0 and 0.1, 1 and 10 µM of Roflumilast). Concentration-response curves for treprostinil were obtained by adding treprostinil (0.1 to 30 µM) alone or in combination with 100 µM Ro-20-1724, 100 µM ibudilast or 5 µM roflumilast. The reaction performed in triplicate was stopped by adding 2.5% perchloric acid together with 0.1 mM (unlabelled) cAMP. [$^3$H]cAMP was isolated by sequential chromatography on Dowex 50W-X4 and neutral alumina columns. The formation of [$^3$H]cAMP was quantified by liquid scintillation counting.

Electrophysiology—Patch Clamp Recordings:

The whole cell patch clamp technique was used for current recordings performed at 22±1.5° C. using an Axoclamp 200B patch clamp amplifier (Axon Instruments). Pipettes had resistances between 1 and 2 MO when filled with the recording pipette solution (composition: 110 mM CsCl, 5 mM EGTA, 2 mM MgCl2, 1 mM K2.ATP, 10 mM Hepes, pH adjusted to 7.2 with CsOH). Voltage-clamp protocols and data acquisition were performed with pclamp 6.0 software (Axon Instruments). Data were low-pass filtered at 2 kHz (−3 dB) and digitized at 10-20 kHz. Cells were continuously superfused with external solution (composition: 145 mM NaCl, 4.5 mM KCl, 2 mM CaCl2, 1 mM MgCl2, 5 mM glucose, 10 mM Hepes, pH adjusted to 7.4 with NaOH). When indicated, the external solution contained Treprostinil (10 µM) or forskolin (5 µM), switching between solutions was achieved by electronically controlled pressure valves.

Accumulation of cAMP in the IB3-1 Cell Line in the Absence and Presence of Phosphodiesterase Inhibitors:

The survey of PDE-isoforms predicts that PDE-inhibitors ought to have a pronounced effect on cAMP accumulation in human bronchial epithelial cells. In addition, this analysis provided evidence for the presence of additional isoforms of phosphodiesterases. Accordingly, the PDE-4 selective inhibitors roflumilast and ibudilast were tested and their effect was compared to that of several additional PDE-inhibitors: RO20-1724, a non-selective PDE-inhibitor with PDE4-preference; dipyridamole, which blocks the equilibrative nucleoside transporter-1 and -2 (ENT1- and ENT2) and, in addition, inhibits PDE5, PDE7A, PDE8A, PDE10A and PDE11 (Soderling et al., 1998; Hetman et al., 2000a&b; Omori & Kotera, 2007). Amrinone, milrinone and cilostazole, which are selective inhibitors of PDE3-isoforms; anagrelide, which inhibits PDE2 and PDE3. Ibudilast is less selective than roflumilast and also inhibits PDE10- and PDE11-isoforms. The approach focused on the regulation of cAMP-levels; hence the cGMP-specific enzymes PDE5, PDE6 and PDE9 were not further considered (Bender & Beavo, 2006; Omori & Kotera, 2007). Cells typically express many isoforms of adenylyl cyclase. In many instances, receptors that are coupled to $G_s$ do not have access to the entire cellular pools of adenylyl cyclases. In contrast, forskolin stimulates all isoforms of adenylyl cyclase. In the absence of phosphodiesterase inhibition, cAMP is rapidly hydrolysed such that it accumulates only to low levels at steady state. Inhibition of phosphodiesterase results in accumulation of cAMP. Roflumilast, ibudilast, dipyridamole and RO20-1724 substantially enhanced the cAMP accumulation triggered by 5 μM forskolin. Roflumilast was the most potent inhibitor and dipyridamol was a less potent inhibitor. Ibudilast and RO20-1724 were more effective than roflumilast. Taken together these data suggested that PDE4-isoforms contributed to a large extent to the hydrolysis of cAMP. If cAMP accumulation was triggered by treprostinil, the concentration-response curve for all inhibitors were shifted to the left. This leftward shift indicates that cAMP generated via receptor stimulation is more readily accessible to degradation by phosphodiesterases. One possible explanation is the anchoring of phosphodiesterases in the vicinity of the receptors (Francis et al., 2011). The higher efficacy of dipyridamole also suggests a possible contribution by PDE8 or PDE10. The main action of the phosphodiesterase inhibitors is to enhance cAMP accumulation: while $E_{max}$ (i.e., the maximum effect increases), the apparent affinity of the agonist (i.e., its $EC_{50}$ is not shifted.

In the absence of an exogenously added agonist (or of forskolin), the PDE-inhibitors do not per se cause any appreciable increase in cAMP accumulation. This is to be expected; the basal activity of adenylate cyclase is very low and it requires input via receptor-dependent activation of $G_s$ to catalyse the formation of cAMP. However, under cell culture conditions—i.e., in defined media—there aren't any agonists present.

PDE-Inhibition Enhances Treprostinil-Induced Cl⁻ Currents Through CFTR:

Because inhibition of PDE4-isoforms enhanced treprostinil-induced cAMP accumulation, this manipulation was predicted to enhance the effect of treprostinil on chloride currents through the cystic fibrosis transmembrane conductance regulator/Cl⁻ channel (CFTR). This was the case: reprostinil caused as sustained activation of CFTR; the resulting outward current can be detected by voltage jumps from −20 to −80 mV. The addition of roflumilast (and of other PDE4 inhibitors such as ibudilast and RO20-1724) caused an additional increase of the current. The current is carried by CFTR, because it is reversibly blocked by the specific inhibitor.

CONCLUSIONS

1) Human airway epithelial cells express several receptors that can be targeted by treprostinil to raise cAMP and thereby activate CFTR in human airway epithelial cells.

2) PDE4-isoforms are present in human airway epithelial cells and PDE4-inhibitors effectively augment the response to treprostinil.

REFERENCES

Aronoff D M, Peres C M, Serezani C H, Ballinger M N, Carstens J K, Coleman N, Moore B B, Peebles R S, Faccioli L H, Peters-Golden M (2007) Synthetic prostacyclin analogs differentially regulate macrophage function via distinct analog-receptor binding specificities. J Immunol 178:1628-1634.

Bender A T, Beavo J A (2006) Cyclic nucleotide phosphodiesterases: molecular regulation to clinical use. Pharmacol Rev 58:488 520

Francis S H, Blount M A, Corbin J D (2011) Mammalian cyclic nucleotide phosphodiesterases: molecular mechanisms and physiological functions. Physiol Rev 91:651-690.

Hetman J M, Soderling S H, Glavas N A, Beavo J A. (2000a) Cloning and characterization of PDE7B, a cAMP-specific phosphodiesterase. Proc Natl Acad Sci USA 97: 472-476

Hetman J M, Robas N, Baxendale R, Fidock M, Phillips S C, Soderling S H, Beavo J A (2000b) Cloning and characterization of two splice variants of human phosphodiesterase 11A. Proc Natl Acad Sci USA 97: 12891-12895

Houslay M D, Schafer P, Zhang K Y (2005) Keynote review: phosphodiesterase-4 as a therapeutic target. Drug Discov Today 10:1503-1519

Omori K, Kotera J (2007) Overview of PDEs and their regulation. Circ. Res. 100:309-327

Nikam V S, Wecker G, Schermuly R, Rapp U, Szelepusa K, Seeger W, Voswinckel R (2011) Treprostinil inhibits adhesion and differentiation of fibrocytes via cAMP and Rap dependent ERK inactivation. Am J Respir Cell Mol Biol 45: 692-703

Soderling S H, Bayuga S J, Beavo J A (1998) Cloning and characterization of a cAMP-specific cyclic nucleotide phosphodiesterase. Proc Natl Acad Sci USA 95:8991-8996.

Wright J M, Zeitlin P L, Cebotaru L, Guggino S E, Guggino W B (2004) Gene expression profile analysis of 4-phenylbutyrate treatment of IB3-1 bronchial epithelial cell line demonstrates a major influence on heat-shock proteins. Physiol Genomics 16:204-211

The invention claimed is:

1. A method of treating cystic fibrosis by improving conductance of chloride by cystic fibrosis transmembrane conductance regulator (CFTR), comprising the step of administering a composition comprising treprostinil or a pharmaceutically acceptable salt, or derivative thereof and at least one phosphodiesterase (PDE) 4 inhibitor to a subject in need thereof to improve conductance of chloride by CFTR in the subject.

2. The method of claim 1, wherein said PDE4 inhibitor is selected from the group consisting of Ro 20-1724, Ibudilast, Roflumilast and its N-Oxide, Cilomilast, BAY 19-8004, CC3, AWD 12-281, SCH 351591, Ciclamilast, Piclamilast, CGH2466, Mesembrine, Rolipram, Luteolin and Drotaverine.

3. The method of claim 2, wherein the PDE4 inhibitor is selected from the group consisting of RO 20-1724, Roflumilast and Ibudilast.

4. The method of claim 1, further comprising a PDE inhibitor selected from the group consisting of a PDE5 inhibitor, a PDE7 inhibitor and a PDE8 inhibitor.

5. The method of claim 4, wherein said PDE5 inhibitor is selected from the group consisting of Avanafil, Lodenafil, Mirodenafil, Sildenafil citrate, Tadalafil, Vardenafil and Udenafil.

6. The method of claim 4, wherein said PDE7 and PDE8 inhibitors are selected from the group consisting of Dipyridamol, BRL50481 and PF-4957325.

7. The method of claim 1, wherein the composition is formulated as a pharmaceutical composition.

8. The method of claim 7, wherein the composition is administered by inhalation administration.

9. The method of claim 1, wherein the composition is administered by a route selected from the group consisting of intravenous administration, subcutaneous administration, and oral administration.

10. The method of claim 9, wherein the composition is formulated for oral administration in a form selected from the group consisting of a sustained release form, a tablet, and a capsule.

11. The method of claim 2, wherein the amount of treprostinil or a pharmaceutically acceptable salt, or derivative thereof which is administered is at least 1.0 ng/kg of body weight.

12. The method of claim 1, wherein the composition comprises treprostinil.

13. The method of claim 1, wherein the treprostinil derivative is selected from the group consisting of an acid derivative of treprostinil, a prodrug of treprostinil, a polymorph of treprostinil, and an isomer of treprostinil.

* * * * *